United States Patent [19]
Pettit et al.

[11] Patent Number: 6,034,065
[45] Date of Patent: Mar. 7, 2000

[54] ELUCIDATION AND SYNTHESIS OF ANTINEOPLASTIC TETRAPEPTIDE PHENETHYLAMIDES OF DOLASTATIN 10

[75] Inventors: George R. Pettit, Paradise Valley, Ariz.; Jozsef Barkoczy, Budapest, Hungary

[73] Assignee: Arizona Board of Regents, Tempe, Ariz.

[21] Appl. No.: 07/985,831

[22] Filed: Dec. 3, 1992

[51] Int. Cl.[7] .................................................. A61K 38/00
[52] U.S. Cl. ............................................. 514/18; 530/330
[58] Field of Search ................................ 530/330; 514/18

[56] References Cited

U.S. PATENT DOCUMENTS 4,978,744  12/1990  Pettit et al. .

OTHER PUBLICATIONS

Correia Pharmac. Ther. vol. 52 (1991) pp. 127–147.
Jacobsen et al. J. of the Natl. Cancer Institute vol. 83 (22) pp. 1672–1677.

*Primary Examiner*—Sheela Huff
*Attorney, Agent, or Firm*—Richard R. Mybeck; Peter B. Scull

[57] ABSTRACT

Dolastatin 10, a linear pentapeptide, has shown potent antineoplastic activity profiles against various experimental cancer systems.

The design and synthesis of structural modifications of dolastatin 10 having significant antineoplastic activity against human cancer cell lines has been accomplished. Members of this group have demonstrated significant antineoplastic activity against selected human cancer cell lines. Especially: Ovarian OVSCAR-3; Central Nervous System ("CNS") SF295; Renal A498; Lung NCI460; Colon KM20L2 and Melanoma SK-MEL-3.

18 Claims, No Drawings

ELUCIDATION AND SYNTHESIS OF ANTINEOPLASTIC TETRAPEPTIDE PHENETHYLAMIDES OF DOLASTATIN 10

This invention relates generally to the field of antineoplastic compounds, and more particularly to the design and synthesis of selected structural modifications of peptides isolated from the Indian Ocean sea hare *Dolabella auricularia*, namely antineoplastic tetrapeptide phenethylamides of dolastatin 10, which have been found to demonstrate effective antineoplastic activity against various human cancer cell lines. Financial assistance for this project was provided by U.S. Government Grant Number OIG-CA44344-01A1-2: the United States Government may own certain rights to this invention.

BACKGROUND OF THE INVENTION

A great number of ancient marine invertebrate species in the Phyla Bryozoa, Mollusca and Porifera were well established in the earth's oceans over one billion years ago. Certainly such organisms had explored trillions of biosynthetic reactions in their evolutionary chemistry to reach present levels of cellular organization, regulation and defense. Marine sponges have changed minimally in physical appearance for nearly 500 million years, suggesting a very effective chemical evolution in response to changing environmental conditions for at least that time period. Some recognition of the potential for utilizing biologically potent marine animal constituents was recorded in Egypt about 2,700 BC, and by 200 BC sea hare extracts were being used in Greece for medicinal purposes. Such considerations, combined with the general observation that marine organisms (especially invertebrates and sharks) rarely develop cancer, led to the first systematic investigation of marine animal and plant anticancer constituents.

By 1968 ample evidence had been obtained, based on the U.S. National Cancer Institute's key experimental cancer systems, that certain marine organisms would provide new and structurally novel antineoplastic and/or cytotoxic agents. Analogous considerations suggested that marine organisms could also provide effective new drugs for other severe medical challenges, such as viral types, that would have eluded discovery by contemporary techniques of medicinal chemistry. Fortunately these expectations have been realized in the intervening period. Illustrative of these successes are discoveries of the bryostatins, dolastatins, and cephalostatins where five members of these series of remarkable anticancer drug candidates are either now in human clinical trial or preclinical development.

As is well known to those presently engaged in medical research, the time between the isolation of a new compound, and its introduction to the market place takes at least several years in the best case, and can take several decades, when an entity to finance the tortuous regulatory trail is slow to appear.

Consequently, industry, in association with the government, has devised a number of qualifying tests which serve two purposes. One aim is to eliminate those substances whose results in the qualifiers unequivocally demonstrate that the further expenditure of funds thereon would be economically counterproductive. The second, and primary aim, is to identify those substances which demonstrate a high likelihood of success and therefore warrant the requisite further investment necessary to obtain the data which is required to meet the various regulatory requirements imposed by those governments which regulate the market place into which such substances will enter.

The present cost of obtaining such data approaches Ten Million Dollars($10,000,000 U.S.) per compound. Economics dictate that such an investment be made only when there is a reasonable opportunity for it to be recovered. This opportunity can only be provided through patent protection. Absent such protection, there will be no such investment, and the advances in such life saving drugs will stop.

Only two hundred years ago, many diseases ravaged humankind. Many of these diseases have been controlled or eradicated. In the development of the means to treat or control these diseases, work with the appropriate common experimental animals was of critical importance. With the various types of cancers, and with the HIV virus, such work is presently ongoing. The research for the treatment of various types of cancer is coordinated by the National Cancer Institute (NCI).NCI, as a government entity, has been charged with assisting anti-cancer research. To establish whether a substance has anti cancer activity, NCI has established a protocol. This protocol, which involves testing a substance against a cell line panel containing 60 human tumor cell lines, has been verified, and is accepted in scientific circles. This protocol, and the established statistical means of evaluating the results obtained therefrom have been amply described in the literature. See e.g. *Principles & Practice of Oncology* PPO Updates, Volume 3, Number 10, October 1989, by Michael R. Boyd, M.D., Ph.D., for a description of the protocol. The statistical analysis is explained in "Display and Analysis of Patterns of Differential Activity of Drugs Against Human Tumor Cell Lines: Development of Mean Graph and COMPARE Algorithm" *Journal of the National Cancer Institute* Reports Vol. 81, No. 14, Pg. 1088, Jul. 14, 1989, by K. D. Paull et al. Both articles are incorporated herein by this reference as if fully set forth.

The Constitution of the United States (Art.1, Sec.8), authorizes Congress to establish the United States Patent and Trademark Office(USPTO) to promote scientific advancement. This obligation can only be fully met when the USPTO accepts current medical and scientific realities in the area of medical research.

The Framers of the Constitution meant for the Patent system to advance, not hamstring, scientific advancement. Cells are alive. The impairment of human tumor cell growth is utility. The sole right obtained by the grant of Letters Patent is that of preventing others from exploiting the subject matter of the patent. The recognition of cell line testing as evidence of antineoplastic activity and hence utility can only aid research in the United States, and will prevent the citizens of the United States from being held hostage by foreign governments or foreign corporations, which could otherwise procede with such projects in a less stringent environment, especially if such research is no longer viable in the United States.

Numerous compounds have been discovered which demonstrate significant antineoplastic activity. As discussed above, many of these compounds have been extracted, albeit with great difficulty, from living creatures such as the sponge or the sea hare. However, once the isolation and testing of such compounds has progressed, a practical problem exists, namely, how to obtain a significant quantity of the compound.

Unlike cinchona bark which was collected to produce quinine, and has an excellent yield, the collection and processing of these compounds in their natural occurring state ranges from the grossly impractical to the utterly impossible. Even ignoring potential ecological effects, the population of such creatures is clearly insufficient.

Accordingly, the elucidation of the absolute structure of such an antineoplastic compound is essential. After the absolute structure has been determined, then means of synthesis must be discovered. Additionally, research is essential to the determination of whether any portion of the naturally occurring compound is irrelevant to the desired properties thereof, which aids in determining the simplest structure which needs to be synthesized in order to obtain the perceived antineoplastic properties.

BRIEF DESCRIPTION OF THE INVENTION

Marine organisms, such as various species of sea hares and sponges continue to produce numerous cyclic and linear peptides that contain unprecedented amino acids which exhibit various important biological activities. Such peptides comprise a promising area of inquiry for the discovery of new anticancer drugs. Several of the dolastatins isolated from the Indian Ocean sea hare *Dolabella auricularia* have proved to be remarkably potent antineoplastic substances representing completely new structural types. Presently, dolastatin 10, a linear pentapeptide, has shown the most potent antineoplastic activity profiles, of the dolastatins, against various experimental cancer systems. Substantial research effort has been devoted to an attempt to better understand the reasons for this unusual efficacy. The absolute configuration of dolastatin 10 has recently been discovered. In addition, investigation as to means of synthesis has progressed. Total synthesis has been accomplished. Earlier, dolastatin 10 chiral isomers were prepared. More recently these experiments were extended to the synthesis of R-Doe-isodolastatin 10. This chiral isomer did not show any significant difference in its human cancer cell line activity as compared to dolastatin 10. That, in turn suggested that the 2-thiazolyl unit might not be important and could be replaced with a simple amide.

Thus the elucidation and synthesis of selected antineoplastic tetrapeptide phenylamides of dolastatin 10 which demonstrate significant antineoplastic activity against a variety of human cancer cell lines, is the object of the subject invention.

This and still further objects as shall hereinafter appear are readily fulfilled by the present invention in a remarkably unexpected manner as will be readily discerned from the following detailed description of an exemplary embodiment thereof.

DESCRIPTION OF THE PREFERRED EMBODIMENT

Marine organisms continue to produce numerous cyclic and linear peptides that contain unprecedented amino acids which exhibit various important biological activities. Such peptides comprise a promising approach to discovery of new anticancer drugs. Several of the dolastatins isolated from the Indian Ocean sea hare *Dolabella auricularia* have proved to be remarkably potent antineoplastic substances representing completely new structural types. Presently dolastatin 10, a linear pentapeptide has shown the most potent antineoplastic activity profiles against various experimental cancer systems. Recently the total synthesis and the absolute configuration of this structurally unique and biologically active peptide was reported. This report has begun to attract increasing interest. Accordingly research on possibly useful structural modifications of dolastatin 10 continued.

Earlier a series of dolastatin 10 chiral isomers was prepared. More recently these experiments were extended to synthesis of R-Doe-isodolastatin 10. This chiral isomer did not show any significant difference in its human cancer cell line activity as compared to dolastatin 10. In turn that suggested that the 2-thiazolyl unit may not be too important and might be replaced.

This synthesis of these new and potent structural modifications took place in many steps. In each case the synthesis began with a solution of [2S-[2R*($\alpha$S*,$\beta$S*)]]-1-[(1,1-dimethylethoxy)carbonyl]-$\beta$-methoxy-$\alpha$-methyl-2-pyrrolidinepropanoic acid (t-Boc-Dolaproine, 1, 0.144 g. 0.5 mmol), which was dissolved in 3 ml dichloromethane distilled from $CaH_2$. To this solution was added the respective amine (2a–c 0.5 mmol) followed by triethylamine (0.077 ml, 0.55 mmol) and diethyl phosphorocyanidate (DEPC, 0.09 ml, 93%, 0.55 mmol, ice bath). The solution was stirred under argon for two hours. The solvent was removed (under vacuum at room temperature) and the residue was chromatographed (silica gel column using hexane-acetone 3:1 as eluent). After the evaporation of solvent from the fractions (selected by TLC) 2 ml dry dichloromethane was added and evaporation was repeated. The residue was dried in a desiccator under vacuum overnight to afford the amide (3a–c), which was generally found as a viscous oil, having the structural formula shown in FIG. 1 below.

A solution of the amide 3a–c (0.2 mmol) in dichloromethane (2 ml) and trifluoroacetic acid (2 ml) was then stirred (ice bath under an argon atmosphere) for two hours. The solvent was removed under reduced pressure and the residue dissolved in toluene. Solvent was again removed in vacuum and this operation was repeated. The residue was dried in a desiccator (under vacuum overnight) to afford the trifluoroacetate salt 4a–c generally found as a viscous oil.

To a solution of the trifluoroacetate salt 4a–c (0.2 mmol) in dichloromethane (2 ml, distilled from $CaH_2$) was added the tripeptide trifluoroacetate salt (5, 0.109 g, 0.2 mmol) followed by triethylamine (0.088 ml, 0.63 mmol) and diethyl phosphorocyanidate (DEPC, 0.036 ml, 93%, 0.22 mmol, ice bath). The solution was stirred under argon for two hours. The solvent was removed (under vacuum at room temperature) and the residue was chromatographed (silica gel column using acetone-hexane 3:2 as eluent). After the evaporation of solvent from the fractions (selected by TLC behaviour) 2 ml of dry dichloromethane was added evaporated. The residue was dried in a desiccator under vacuum overnight to yield a white fluffy solid.

The following examples exemplifying the preferred embodiment of the subject invention are offered to assist in the understanding of the subject invention.

EXAMPLE I

Synthesis of Amides 3a–c. General Procedure A

To a solution of [2S-[2R* ($\alpha$S*,$\beta$S*)]]-1-[(1,1-dimethylethoxy)carbonyl]-methoxy-$\alpha$-methyl-2-pyrrolidinepropanoic acid (t-Boc-Dolaproine, 1, 0.144 g, 0.5 mmol) in dichloromethane (3 ml, distilled from $CaH_2$) was added the respective amine (2a–c 0.5 mmol) followed by triethylamine (0.077 ml, 0.55 mmol) and diethyl phosphorocyanidate (DEPC, 0.09 ml, 93%, 0.55 mmol, ice bath) and the solution was stirred under argon for two hours. The solvent was removed (under vacuum at room temperature) and the residue was chromatographed (silica gel column using hexane-acetone 3:1 as eluent).After the evaporation of solvent from the fractions (selected by TLC) 2 ml dry dichloromethane was added and evaporation was repeated. The residue was dried in a desiccator under vacuum overnight to afford the amide (3a–c), generally found as a viscous oil, having the structural formula shown below.

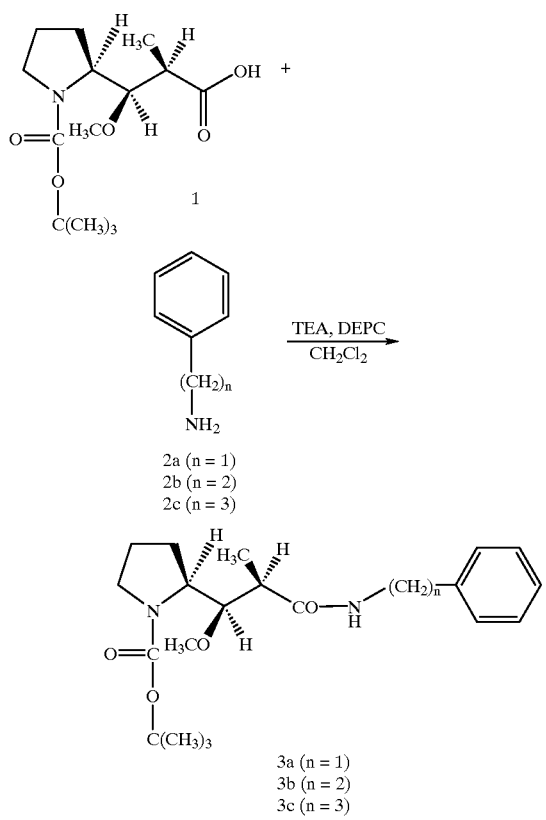

EXAMPLE Ia

Compound 3a [2S-[2R*[1S*, 2S*]]]-2-[1-methoxy-2-methyl-3-oxo-3-benzylamino-propyl]-1-pyrrolidinecarboxylic acid, 1,1-dimethylethylester (3a), was synthesized from t-Boc-Dolaproine (1) and benzylamine (2a) according to General Procedure A as set forth in EXAMPLE I with the following results.

Yield 3a: 0.176 g (81%) $[\alpha]_D^{25}$=−42.2 (c=2.22 in CHCl$_3$) Anal. Calcd for $C_{21}H_{32}N_2O_4$ M. w.: 376.488

EXAMPLE Ib

Compound 3b [2S-[2R*[1S*, 2S*]]]-2-[1-methoxy-2-methyl-3-oxo-3-[[2-phenyl-ethyl]amino]propyl]-1-pyrrolidinecarboxylic acid, 1,1-dimethylethylester (3b) was synthesized from t-Boc-Dolaproine (1) and phenethylamine (2b) according to General Procedure A set forth in EXAMPLE I, with the following results.

Yield 3b: 0.153 g (78%) $[\alpha]_D^{25}$=−37.5 (c 0.96, CHCl$_3$) Anal. Calcd for $C_{22}H_{34}N_2O_4$, M. w.:390.514

EXAMPLE Ic

Compound 3c[2S-[2R*[1S*, 2S*]]]-2-[1-methoxy-2-methyl-3-oxo-3-[[3-phenyl-propyl]amino]propyl]-1-pyrrolidinecarboxylic acid, 1,1-dimethylethylester (3c) was synthesized from t-Boc-Dolaproine (1) and 3-phenyl-1-propylamine (2c) according to General Procedure A as set forth in EXAMPLE I with the following results.

Yield 3c: 0.153 g (75%) $[\alpha]_D^{25}$=−43 (c 1.8, CHCl$_3$) Anal. Calcd for $C_{23}H_{36}N_2O_4$, M. w.: 404.54

EXAMPLE II

Synthesis of Peptides 6a–c (FIGS. 2. and 3a.). General Procedure B.

A solution of the selected amide 3a–c (0.2 mmol) in dichloromethane (2 ml) and trifluoroacetic acid (2 ml) was stirred (ice bath under an argon atmosphere) for two hours. The solvent was removed under reduced pressure and the residue dissolved in toluene. Solvent was again removed in vacuum and this operation was repeated. The residue was dried in a desiccator (under vacuum overnight) to afford the respective trifluoroacetate salt 4a–c as a viscous oil.

To a solution of the selected trifluoroacetate salt 4a–c (0.2 mmol) in dichloromethane (2 ml, distilled from CaH$_2$) was added the tripeptide trifluoroacetate salt (5, 0.109 g, 0.2 mmol) followed by triethylamine (0.088 ml, 0.63 mmol) and diethyl phosphorocyanidate (DEPC, 0.036 ml, 93%, 0.22 mmol, ice bath). The solution was stirred under argon for two hours. The solvent was removed (under vacuum at room temperature) and the residue was chromatographed (silica gel column using acetone-hexane 3:2 as eluent). After the evaporation of solvent from the fractions (selected by TLC behaviour) 2 ml of dry dichloromethane was added evaporated. The residue was dried in a desiccator under vacuum overnight to yield a white fluffy solid.

FIG. 2. Trifluoroacetate salt 4a–c

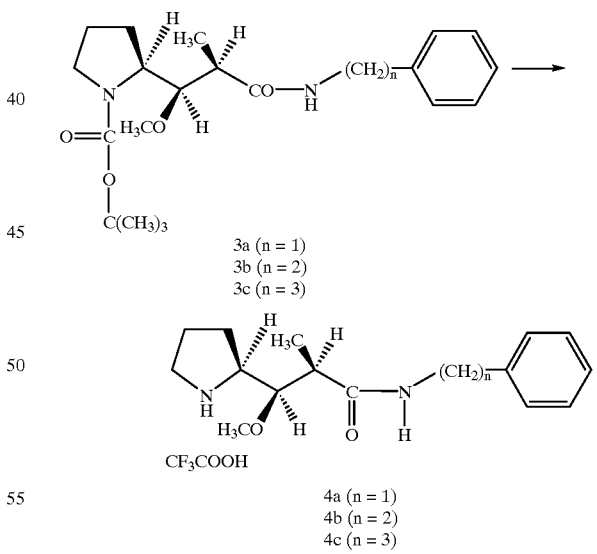

FIG. 3a. Synthesis of Peptides 6a–c

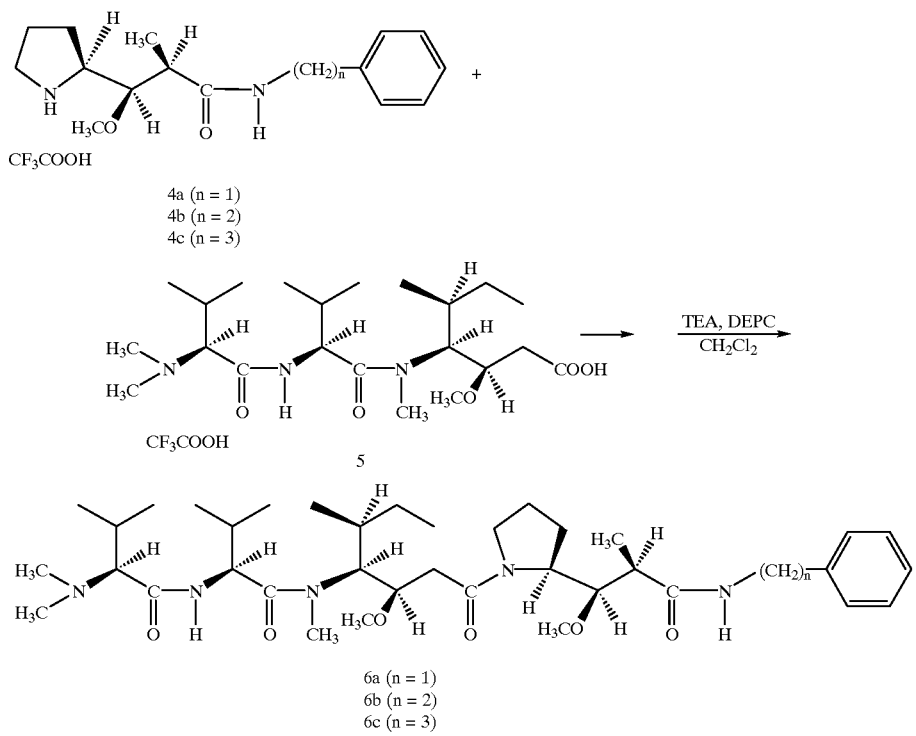

6a (n = 1)
6b (n = 2)
6c (n = 3)

EXAMPLE IIa

Compound 6a [2S-[1[1R*(R*),2S*],2R*[1S*,2S*]]]-N,N-dimethyl-L-valyl-N-[2-methoxy-4-[2-[1-methoxy-2-methyl-3-oxo-3-benzylamino-propyl]-1-pyrrolidinyl-1-(methylpropyl)-4-oxobutyl]-N-methyl-L-valineamide (6a) was synthesized from trifluoroacetate salt 4a (from amide 3a) and tripeptide trifluoroacetate salt 5, in accordance with General Procedure B, as set forth in EXAMPLE II, with the following results.

Yield 6a: 112 mg (81%) M. p.: 88–93 °C. $[\alpha]_D^{25} = -40$ (c=0.65 in CHCl$_3$) Anal. Calc. : C$_{38}$H$_{65}$N$_5$O$_6$ Mw.: 687.94

EXAMPLE IIb

Compound 6b [2S-[1[1R*(R*),2S*],2R*[1S*,2S*]]]-N,N-dimethyl-L-valyl-N-[2-methoxy-4-[2-[1-methoxy-2-methyl-3-oxo-3-[[2-phenyl-ethyl]amino]propyl]-1-pyrrolidinyl-1-(methylpropyl)-4-oxobutyl]-N-methyl-L-valineamide (6b) was synthesized from trifluoroacetate salt 4b (from amide 3b) and tripeptide trifluoroacetate salt 5, in accordance with General Procedure B, as set forth in EXAMPLE II, with the following results.

Yield 6b: 0.115 (82%) g M. p.: 73–79° C. $[\alpha]_D^{25} = -36.9$ (c 0.74, CH$_3$OH) Anal. Calcd for C$_{39}$H$_{67}$N$_5$O$_6$, M. w.: 701.966

EXAMPLE IIc

Compound 6c [2S-[1[1R*(R*),2S*],2R*[1S*,2S*]]]-N,N-dimethyl-L-valyl-N-[2-methoxy-4-[2-[1-methoxy-2-methyl-3-oxo-3-[[3-phenyl-propyl]amino]propyl]-1-pyrrolidinyl-1-(methylpropyl)-4-oxobutyl]-N-methyl-L-valineamide (6c) was synthesized from trifluoroacetate salt 4c (from amide 3c) and tripeptide trifluoroacetate salt 5 in accordance with General Procedure B, as set forth in EXAMPLE II, with the following results.

Yield 6c: 112 mg (78%) M. p.: 106–109° C. $[\alpha]_D^{25} = -73$ (c=0.1 in CHCl$_3$) Anal. Calc.: C$_{40}$H$_{69}$H$_5$O$_6$ Mw.: 715.992

The structural modifications of dolastatin 10 whose design and synthesis are described herein were evaluated for antineoplastic activity. This evaluation was conducted using the standard protocols established by National Cancer Institute (NCI) as described above. These protocols do evaluate whether the substances in question have antineoplastic activity against certain human cancer cell lines derived from human cancer patients. Substantial activity was found in those compounds tested. The antineoplastic activity of the compounds is reported below in Table 1. The results of the 60 cell line NCI in vitro testing of compound 6b conducted Jun. 22, 1992, is reported below in Table 2.

TABLE 1

Biological activity of Peptides 6a–c

| Cell type | Cell line | 6 a | 6 b | 6 c |
|---|---|---|---|---|
| Mouse leukemia cell ED-50 (mg/ml) | P-388 | 0.003780 | 0.00050 | 0.000440 |
| Ovarian | OVCAR-3 | <0.0001 | 0.000004 | 0.000180 |
| CNS | SF-295 | <0.0001 | 0.000014 | 0.000280 |

TABLE 1-continued

Biological activity of Peptides 6a–c

| | Cell type | Cell line | 6 a | 6 b | 6 c |
|---|---|---|---|---|---|
| Human cancer cell GI-50 (μg/ml) | Renal | A498 | <0.0001 | 0.000013 | 0.000390 |
| | Lung-NSC | NCI-460 | <0.0001 | 0.000005 | 0.000310 |
| | Colon | KM20L2 | <0.0001 | 0.000005 | 0.000330 |
| | Melanoma | SK-MEL-3 | <0.0001 | 0.000012 | 0.000310 |
| | Ovarian | OVCAR-3 | <0.0001 | 0.000027 | 0.000540 |
| | CNS | SF-295 | <0.0001 | 0.000042 | 0.000790 |
| Human cancer cell TGI (μg/ml) | Renal | A498 | <0.0001 | <0.0001 | <0.01 |
| | Lung-NSC | NCI-460 | <0.0001 | <0.0001 | <0.01 |
| | Colon | KM20L2 | <0.0001 | <0.0001 | <0.01 |
| | Melanoma | SK-MEL-3 | <0.0001 | <0.0001 | <0.01 |
| | Ovarian | OVCAR-3 | <0.0001 | <0.0001 | <0.01 |
| | CNS | SF-295 | <0.0001 | <0.0001 | <0.01 |
| Human cancer cells LC-50 (μg/ml) | Renal | A498 | <0.0001 | <0.0001 | <0.01 |
| | Lung-NSC | NCI-460 | <0.0001 | <0.0001 | <0.01 |
| | Colon | KM20L2 | <0.0001 | <0.0001 | <0.01 |
| | Melanoma | SK-MEL-3 | <0.0001 | <0.0001 | <0.01 |

From the foregoing, it is readily apparent that new and useful embodiments of the present invention have been herein described and illustrated which fulfill all of the aforestated objectives in a remarkably unexpected fashion. It is of course understood that such modifications, alterations and adaptations as may readily occur to the artisan confronted with this disclosure are intended within the spirit of this disclosure which is limited only by the scope of the claims appended hereto.

We claim:

1. A composition of matter comprising a compound having the general structure:

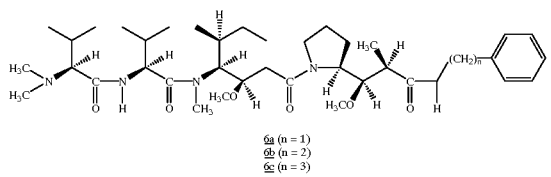

wherein n is selected from the group consisting of 1, 2, and 3.

2. A method of inhibiting the growth of abnormal human cells selected from the group consisting of leukemia, non-small cell lung cancer, colon cancer, CNS cancer, melanoma, ovarian cancer, and renal cancer; comprising engaging said cells with a growth inhibitory amount of a compound having the following structural formula:

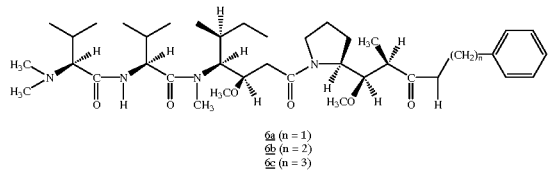

6a (n = 1)
6b (n = 2)
6c (n = 3)

wherein n is selected from the group consisting of 1, 2, and 3.

3. A method according to claim 2 wherein said abnormal cells are selected from the group of abnormal cell lines having the following NCI cell line designations: P-388, OVCAR-3, SF-295, A498, NCI 460, KM20L2, and SK-MEL-3.

4. A method according to claim 3 wherein n=1.

5. A method according to claim 3 wherein n=3.

6. A method according to claim 2 wherein n=2.

7. A method according to claim 6 wherein said abnormal human cells are selected from the group consisting of leukemia cell lines having the NCI Cell Line designations: CCRF-CEM, HL-60(TB), K-562, MOLT-4, RPM-8226 and SR.

8. A method according to claim 6 wherein said abnormal human cells are selected from the group consisting of Non-Small Cell Lung Cancer Cell Lines having the NCI Cell Line designations: A549/ATCC, EXVX, HOP-62, HOP-92, NCI-H226, NCI-H23, NCI-H460, NCI-H522, and LXFL-529.

9. A method according to claim 6 wherein said abnormal cells are selected from the group consisting of Colon Cancer Cell Lines having the NCI Cell Line designations: C0L0 205, DLD-1, HCT-116, HCT-15, KM20L2 and SW-620.

10. A method according to claim 6 wherein said abnormal cells are selected from the group consisting of CNS Cancer Cell Lines having the NCI Cell Line designations: SF-268, SF-539, SNB-19, SNB-75, SNB-78 and U251.

11. A method according to claim 6 wherein said abnormal cells are selected from the group consisting of Melanoma Cancer Cell Lines having the NCI Cell Line designations: LOX1MV1, MALMB-3M, M14, M19-MEL, SK-MEL-2, SK-MEL-5, and UACC-62.

12. A method according to claim 6 wherein said abnormal cells are selected from the group consisting of Ovarian Cancer Cell Lines having the NCI Cell Line designations: 1GROV1, OVCAR-5, OVCAR-8, and SK-OV-3.

13. A method according to claim 6 wherein said abnormal cells are selected from the group consisting of Renal Cancer Cell Lines having the NCI Cell Line designations: 786-O, ACHN, CAK1-1, RXP-393, SN12C, TK-10, and UO-31.

14. A method according to claim 3 wherein n=2.

15. A composition of matter according to claim 1 wherein n=1.

16. A composition of matter according to claim 1 wherein n=2.

17. A composition of matter according to claim 1 wherein n=3.

18. A pharmaceutical preparation comprising a compound having the structure set forth in claim 1.

* * * * *

UNITED STATES PATENT AND TRADEMARK OFFICE
CERTIFICATE OF CORRECTION

PATENT NO. : 6,034,065  
APPLICATION NO. : 07/985831  
DATED : March 7, 2000  
INVENTOR(S) : Pettit et al.

Page 1 of 1

It is certified that error appears in the above-identified patent and that said Letters Patent is hereby corrected as shown below:

- Column 11, line 57, claim 1, replace the chemical structure with the one shown below:

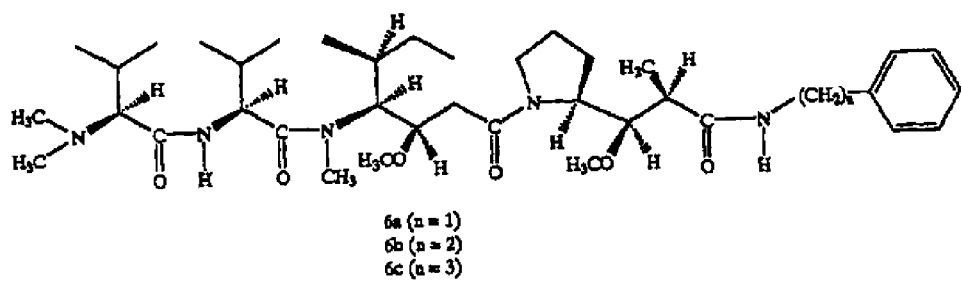

- Column 13, line 1, claim 2, replace the chemical structure with the one shown below:

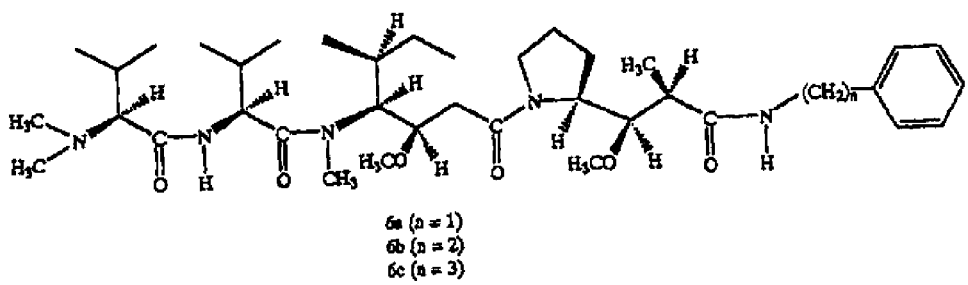

Signed and Sealed this

Tenth Day of February, 2009

JOHN DOLL  
*Acting Director of the United States Patent and Trademark Office*

```
                        SEQUENCE LISTING (1) GENERAL INFORMATION:

(iii) NUMBER OF SEQUENCES: 3

(2) INFORMATION FOR SEQ ID NO: 1:

(i) SEQUENCE CHARACTERISTICS:
           (A) LENGTH: 4 amino acid residues
           (B) TYPE: amino acid
           (D) TOPOLOGY: linear (ii) MOLECULE TYPE:
           (A) DESCRIPTION:  Linear tetrapeptideamide (iii) HYPOTHETICAL:  no (iv) ANTI-SENSE:    no (vi) ORIGINAL SOURCE: synthesis (ix) FEATURE:
           (A) NAME/KEY: [2S-[1[1R*(R*),2S],2R*[1S*,2S*]]]-
               N,N-dimethyl-L-valyl-N-[2-methoxy-4-[2-[1-methoxy-2-
               methyl-3-oxo-3-benzyl-amino-propyl]-1-pyrrolidinyl-
               1-(methylpropyl)-4-oxobutyl]-N-methyl-L-valineamide
           (B) IDENTIFICATION METHOD:  by experiment using
               high resolution nuclear magnetic resonance and mass
               spectral techniques
           (C) OTHER INFORMATION: this tetrapeptideamide is
               cell growth inhibitory peptide derivative (xi) SEQUENCE DESCRIPTION: SEQ ID NO: 1:

Xaa Val Xaa Xaa (2) INFORMATION FOR SEQ ID NO: 2:

(i) SEQUENCE CHARACTERISTICS:
           (A) LENGTH: 4 amino acid residues
           (B) TYPE: amino acid
```

```
            (D) TOPOLOGY: linear (ii) MOLECULE TYPE:
         (A) DESCRIPTION: Linear tetrapeptideamide (iii) HYPOTHETICAL: no (iv) ANTI-SENSE:    no (vi) ORIGINAL SOURCE: synthesis (ix) FEATURE:
         (A) NAME/KEY: [2S-[1[1R*(R*),2S],2R*[1S*,2S*]]]-N,N-dimethyl-
             L-valyl-N-[2-methoxy-4-[2-[1-methoxy-2-methyl-3-oxo-3-[
             [2-phenyl-ethyl]amino]propyl]-1-pyrrolidinyl-1-
             (methylpropyl)-4-oxobutyl]-N-methyl-L-valineamide
         (B) IDENTIFICATION METHOD: by experiment using high
             resolution nuclear magnetic resonance and mass spectral
             techniques
         (C) OTHER INFORMATION: this tetrapeptideamide is
             cell growth inhibitory peptide derivative (xi) SEQUENCE DESCRIPTION: SEQ ID NO: 2:

Xaa Val Xaa Xaa (2) INFORMATION FOR SEQ ID NO: 3:

(i) SEQUENCE CHARACTERISTICS:
        (A) LENGTH: 4 amino acid residues
        (B) TYPE: amino acid
        (D) TOPOLOGY: linear (ii) MOLECULE TYPE:
         (A) DESCRIPTION: Linear tetrapeptideamide (iii) HYPOTHETICAL: no (iv) ANTI-SENSE:    no (vi) ORIGINAL SOURCE: synthesis (ix) FEATURE:
         (A) NAME/KEY: [2S-[1[1R*(R*),2S],2R*[1S*,2S*]]]-
             N,N-dimethyl-L-valyl-N-[2-methoxy-4-[2-[1-methoxy-2-
             methyl-3-oxo-3-[[3-phenyl-propyl]amino]propyl]-1-
             pyrrolidinyl-1-(methylpropyl)-4-oxobutyl]-N-methyl-
             L-valineamide
         (B) IDENTIFICATION METHOD: by experiment using
             high resolution nuclear magnetic resonance and mass
             spectral techniques
         (C) OTHER INFORMATION: this tetrapeptideamide is
             cell growth inhibitory peptide derivative (xi) SEQUENCE DESCRIPTION: SEQ ID NO: 3:

Xaa Val Xaa Xaa
```